United States Patent [19]

Anderson et al.

[11] 4,413,630

[45] Nov. 8, 1983

[54] SECTOR SCANNER DISPLAY AND RECORDING SYSTEM FOR ULTRASONIC DIAGNOSIS

[75] Inventors: Weston A. Anderson; Lloyd D. Clark, both of Palo Alto; William L. Beaver, Los Altos Hills, all of Calif.

[73] Assignee: Diasonics Cardio/Imaging, Inc., Salt Lake City, Utah

[21] Appl. No.: 239,251

[22] Filed: Mar. 2, 1981

Related U.S. Application Data

[60] Division of Ser. No. 914,323, Jun. 12, 1978, Pat. No. 4,274,422, which is a continuation of Ser. No. 673,500, Apr. 5, 1976, abandoned.

[51] Int. Cl.³ ............................................. A61B 10/00
[52] U.S. Cl. ................................... 128/661; 128/712
[58] Field of Search ................ 128/660, 661, 710–712, 128/700

[56] References Cited

U.S. PATENT DOCUMENTS

| 3,774,479 | 7/1973 | Stein et al. | 128/661 |
| 3,793,626 | 2/1974 | Zambuto | 128/710 |
| 3,995,259 | 11/1976 | Harris et al. | 128/712 |

OTHER PUBLICATIONS

King, D. L., "Real-Time Cross Sectional UTS Imaging of the Heart Using a Linear Array Multi-Element Transducer", Jrnl. Chim. UTS V. (#3, pp. 196-200, 1974).

Takemura, Y. et al., "Highspeed UTS-Cardiotomograph, Sonolayerograph Model SSL-51H", Toshika Review, No. 98, pp. 25-30, Jul.-Aug. 1975.

Primary Examiner—Lee S. Cohen
Assistant Examiner—Francis J. Jaworski
Attorney, Agent, or Firm—Blakely, Sokoloff, Taylor & Zafman

[57] ABSTRACT

Improvements are disclosed in an ultrasonic display and recording system of the type utilized in diagnostic medicine with particular applicability in cardiovascular diagnosis. The system includes a multi-element transducer for generating and receiving ultrasonic energy which is propagated into and reflected back from the cardiovascular region of the patient being examined, and also includes means for generating a two-dimensional real time display and/or image of the zone of examination. TM recording means are associated with the system and may be actuated to effect a TM recording corresponding to a preselected region of the real time image being observed. An ECG output signal is also displayed in real time with the two-dimensional image, and photographs of the displays may be produced at selected points in the ECG cycle in accordance with a setting made by the system operator. The system includes provision for generating video recordings; and means for imposing various identification and time data upon the displays.

17 Claims, 7 Drawing Figures

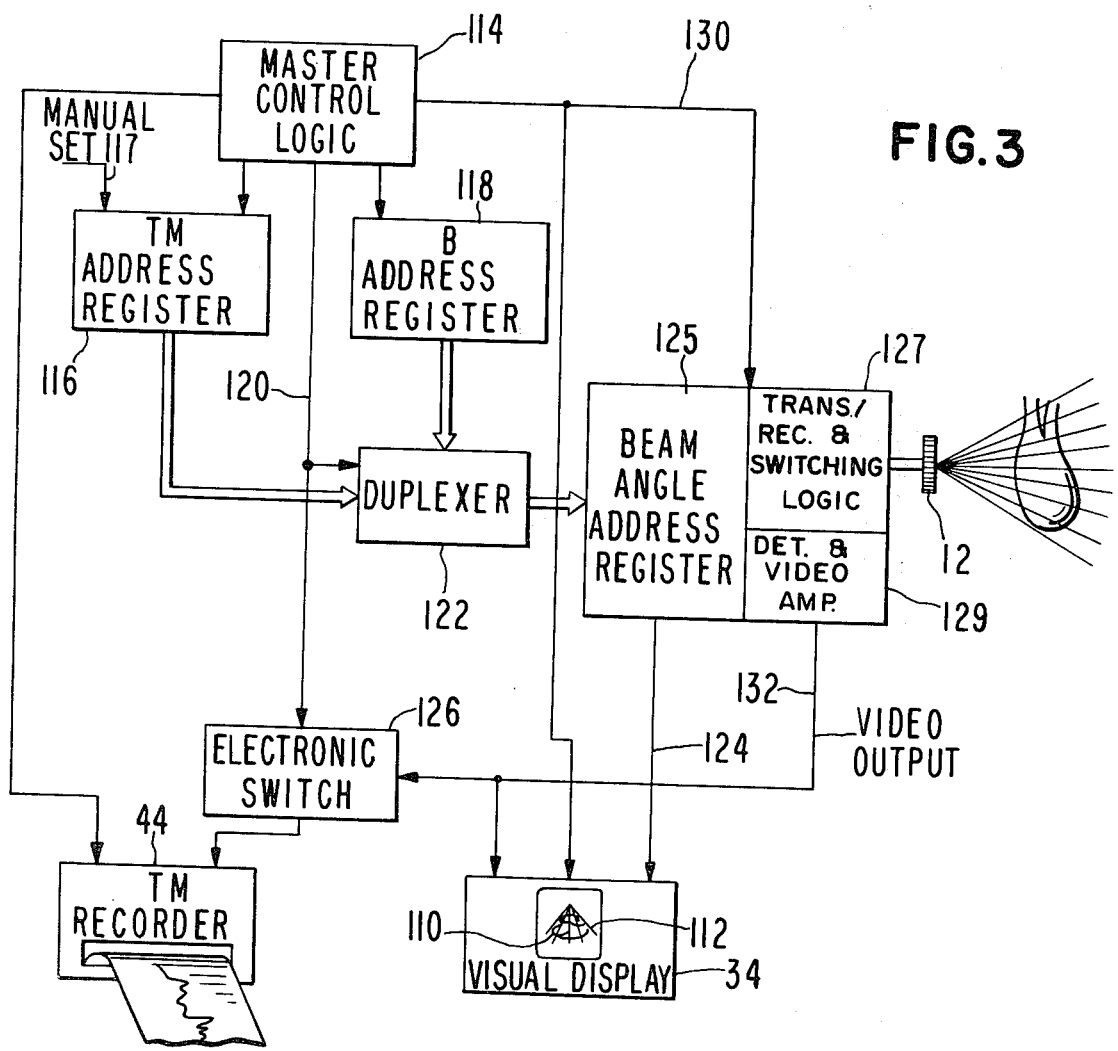

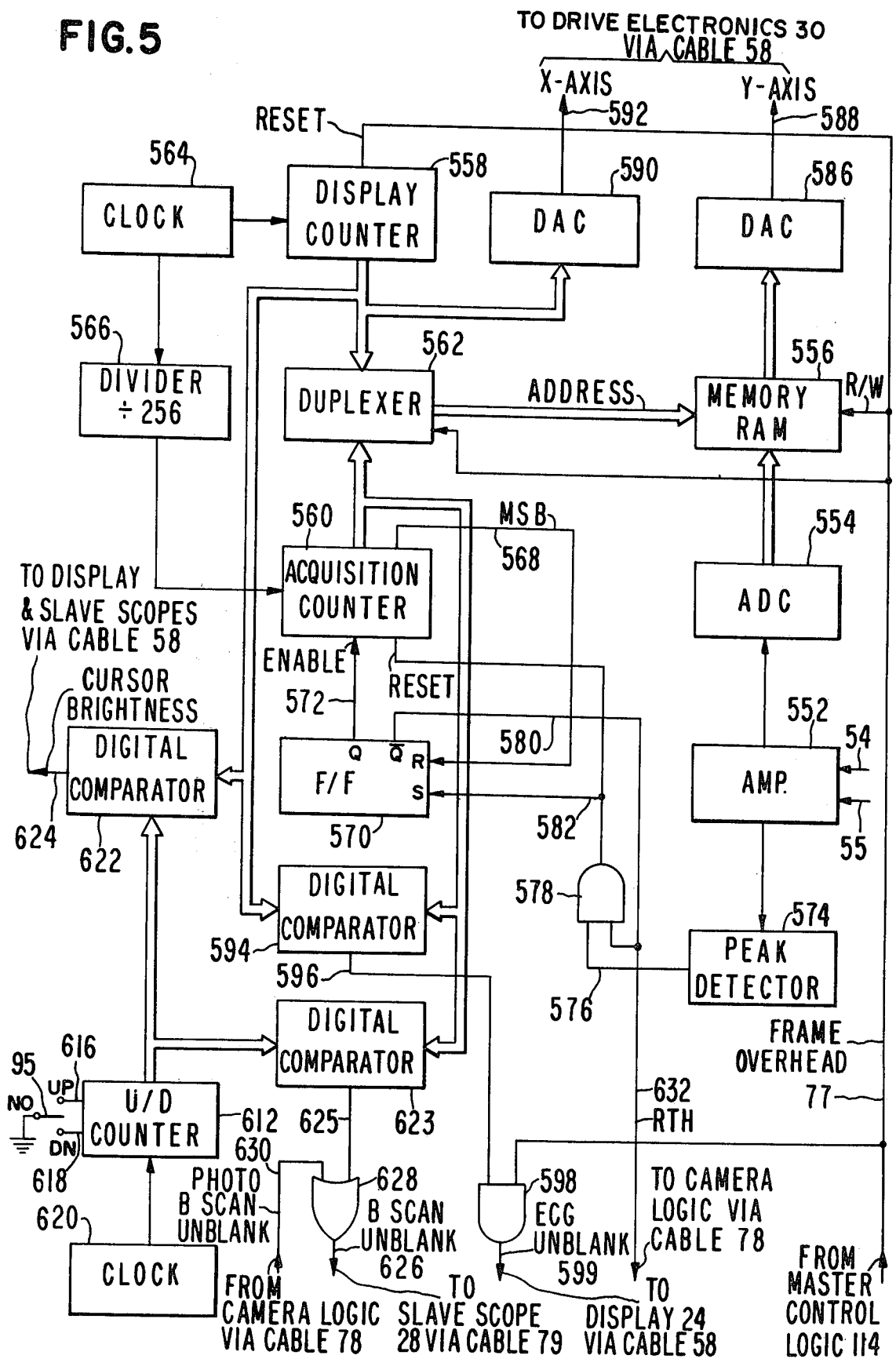

SECTOR SCANNER DISPLAY AND RECORDING SYSTEM FOR ULTRASONIC DIAGNOSIS

This is a division of application Ser. No. 914,323 filed June 12, 1978, now U.S. Pat. No. 4,274,422, which in turn is a continuation of Application Ser. No. 673,500, filed Apr. 5, 1976, now abandoned.

BACKGROUND OF INVENTION

This invention relates generally to apparatus and methodology for effecting medical diagnosis, and more specifically relates to systems and methodology utilizing ultrasonic techniques for such purposes.

Over the course of the last two to three decades, ultrasonic technology has played an ever-increasing role in medical diagnostics. An area of special interest for present purposes is the use of such technology for identifying and examining cardiac structures. As far back as at least 1953, Edler and Hertz described techniques wherein echoes provided by structures within the heart, could be converted into curves indicative of the movements of portions of the said structure. Techniques of this type have generally been identified under the term "echocardiography" or by the term "TM" (Time-Motion) scanning. Pursuant to these techniques, a narrow ultrasonic sound beam is projected into the regions of the heart from a surface transducer that may, e.g., be positioned as to propagate the beam between the ribs. As a pulse of ultrasonic energy is propogated inwardly through the various structures, including heart wall, valves, and the like, some of the energy is reflected back toward the transducer at the boundaries between the various structures. This reflected energy is then detected, amplified and, as desired, displayed on an oscilloscope or recorded on a strip chart.

The type of information secured by the aforementioned techniques can be of great diagnostic value since the structures being examined change in a characteristic way in certain diseases of the heart, and a skilled physician can readily determine the presence of such changes from examination of a properly obtained display or recording of the type mentioned.

Insofar as the TM scan is concerned, it may be observed that up until recently, a major problem inherent in the applicable apparatus was that the operator was, in essence, "flying blind". This is to say that the only information that such operator had regarding whether the transducer was properly oriented for the structure that he was trying to observe, was obtained by looking at the data that was being recorded on the display scope or on the recorder. Pursuant to such approach, the operator was required to tilt or angulate the transducer to cover and seek out a range of structures on which he desires to obtain recordings. Thus, the only feedback he had regarding whether the recording being made actually included the structures desired to be observed was obtained after the fact.

Recently apparatus has been reported wherein a TM scan may be obtained from a B-scan obtained from a near field array. The difficulty is that the TM scan images obtained from a near field array are not in a form familiar to diagnosticians and for such reasons are not readily correlated to the structures examined.

It may nextly be noted that a number of ultrasonic imaging systems have recently been reported—and in some instances, have become available for use by researchers—which systems enable a two-dimensional image, e.g., of a cardiac structure, to be generated and observed in real time. A system of this type utilizing phased array principles to steer and focus an ultrasound beam provided by an array of transducers, is described by Thurston and von Ramm in "A New Ultrasound Technique Employing Two-Dimensional Electronic Beam Steering", appearing in *Acoustical Holography*, Volume 5, P. S. Green, Editor, Plenum Press, 1974. Additional aspects of systems based upon such apparatus are set forth at Volume 6 of the mentioned *Acoustical Holography* series at page 91, in an article by von Ramm, Thurston, and Kisslo entitled "Cardiovascular Diagnosis with Real Time Ultrasound Imaging". Reference may also be usefully made to J. C. Somer, "Electronic Sector Scanning for Ultrasonic Diagnosis", appearing at page 153 of *Ultrasonics* for July, 1968.

The real time imaging systems above mentioned, and others as have been recently described by additional researchers, have indeed provided useful new tools for the medical diagnostician, in that, for the first time, it has become practical to directly observe an extended expanse of the heat functioning in real time, or substantially simultaneously with the functions occurrence. At the same time, however, such systems have represented but an initial approach to an extremely complex diagnostic environment; and the reported systems have been markedly lacking in the sophistication and flexibility that the diagnostician requires. Numerous of these prior art systems, for example, have generated low resolution in the images thereby provided, and have not included capabilities for manipulating the image to concentrate upon or examine certain specified regions within the heart or associated cardiovascular structures. Of perhaps greater significance is the fact that these prior art devices have failed to enable a diagnostic interrelationship between the B-mode display which they provide, and the various additional diagnostic read-outs commonly employed by the cardiologist—including, for example, the well-known ECG, the phonocardiogram, and the already mentioned TM mode display and recordings.

In accordance with the foregoing, it may be regarded as one object of the present invention, to provide a display and recording system for ultrasonic diagnosis; which system is particularly applicable to cardiology; and which is capable of directly displaying for operator investigation a high resolution and readily manipulatable real time image of cardiac structures.

It is a further object of the present invention, to provide a system of the foregoing type, which includes means for enabling simultaneous or independent display of an ECG or a phonocardiogram, and in a form which enables the system operator to readily observe such data.

It is a yet further object of the present invention, to provide a diagnostic system, wherein ultrasonic methodology is used to visualize in a fan shaped display in real time a cardiac structure or the like, thereby enabling a so-called B-mode display of such structures; which system further includes means for rapidly and automatically effecting a TM-mode read-out or scan of the portion of the cardiac structure then being displayed.

It is a still additional object of the present invention, to provide an ultrasonic imaging system particularly adapted to the generation of real time B-mode displays of cardiac structures; which system includes means for automatically securing photographs of the said B-mode display; and wherein photographing of said display may be directly correlated with a timing point referenced to an ECG being generated by the cardiac structure being observed, thereby enabling the cardiac structure to be photographically recorded at the precise point in the cardiac cycle which is deemed of interest to the diagnostician.

A still further object of the present invention, is to provide an ultrasonic diagnosing system of the aforementioned type which, in addition to including means for obtaining photographs of the real time B-mode display, includes operator-actuated means for superimposing alphanumeric and timing information upon the display, in consequence of which the resultant photographs are directly provided with precise data useful for record-keeping or other purposes, including, e.g., medico-legal or regulatory purposes.

A yet further object of the present invention, is to provide an ultrasonic disposing system of the aforementioned type, which in addition to including means for producing a video recording of the real time B-made display, includes capability for superimposing precise time information on the displays being recorded, to thereby facilitate and assure accurate analysis of the recordings.

SUMMARY OF INVENTION

Now in accordance with the present invention, the foregoing objects and others as will become apparent in the course of the ensuing specification are achieved in an ultrasonic display and recording system, which in addition to providing a high resolution and highly manipulatable real-time image of cardiac structures or the like, includes a wide variety of additional features, which so interact with the real-time imaging capabilities cited, as to enable vast augmentation in the diagnostic capabilities of the system.

The transducer utilized with the system of the invention preferably comprises a phased array consisting of a plurality of elements arranged in a compact linear array. The transducer is connected to a suitable transmitter and receiver, and the transmitted pulses are so phased as to steer the emitted sound beam in the desired direction. Adjustable delays provided in each receiver channel enhance the reception from the same direction as the transmitted sound beam. By suitably controlling the timing of the voltages applied to the transducer elements and the adjustable delays of the separate receiver channels, the beam can be steered to any desired angle of a fan-shaped sector. Operation of the steered array is such that a plurality of radial lines defining the fan-shaped sector are successively generated with a relatively high number of such radial lines, typically of the order of 64 such lines, being utilized in the course of generating the entire sector. The set of such lines are generated over a short period, typically of the order of 1/30th of a second, whereby the corresponding display on the system cathode-ray tube (CRT) is a high resolution, substantially real time (or "high speed") image of the heart and related cardiovascular structures, the said visualization being in the so-called B-mode, i.e., one wherein variations of the acoustical impedance of the tissue are translated into brightness variations on the CRT screen.

The use of the phased array sector scanner offers important advantages in the visualization and measurement of cardiovascular structures. It permits visualization of the cardiac area through the relatively small access that is available between the ribs. It also offers the cardiologist a small light-weight transducer similar to those used in prior art TH-mode instruments. In prior art TM instruments the cardiologist would examine the various cardiac structures by angulating the transducer to send the beam successively through the structures of interest and these are then recorded on a TM-mode strip chart recorder. In accordance with this invention, the same type of display is obtained automatically by permitting the cardiologist to obtain a TM-mode scan of the two-dimensional picture being observed on the CRT screen.

Prior art linear-array near-field ultrasonic scanners do not permit the same display to be translated into a TM-mode scan since they display the B-scan picture in a rectangular format rather than the angular format obtained in the sector scanner. Thus, one of the advantages of the present invention is that it permits a standard TM-mode display to be obtained in the usual format as obtained in the prior art TM-mode recordings with the advantages of being able to visualize the structures in their actual configurations before and in fact while the TM recording is made.

Means are provided in the system for varying the sector size of the fan-shaped area being examined by the transducer, to achieve a desired angular configuration varying e.g. between 20 and 80 degrees. Since the same number of scan lines are utilized in each instance, such feature enables increased resolution where a particular portion of the image is deemed of special interest.

In another aspect of the invention, means are provided which vary the repetition rate of scan lines as to enable depth control of the displayed sector scan. By this technique, examination of less deep portions of the cardiac structure can be achieved with a corresponding increase in the line density. For example, when examining structures near the maximum range of 21 cm in the described device a total of 64 lines are used. By restricting the maximum depth to 7 cm in said device a total of 192 lines might be used, providing superior sensitivity while examining infants for example.

In other aspects of the invention, the data being processed by the transducer-linked receiver may be varied to compress portions of same, i.e., to enable non-linear processing; and the system may include means for rejecting signals below a certain amplitude, i.e., to enable noise rejection.

In a further aspect of the control enabled by the system at the sector-shaped display, means are provided by varying the gain of the receiver at various sectors of the examination zone. In this manner, it is possible to compensate for regions of greater attenuation that may occur in certain regions of the body.

As already mentioned the present system provides the direct visual display on a CRT accessible for operator viewing. A slave scope is driven in synchronism with the visual display and photographic camera means are positioned to enable photographs to be directly obtained from the slave scope. The slave scope is also associated with a vidicon, the outputs of which are provided to both a video recorder and to a video monitor—for enabling auxiliary or remote viewing of the display.

The output from the transducer receiver is also provided to a TM-mode recorder, which enables TM-mode strip records to be directly obtained from the present apparatus. An especially significant aspect of this arrangement is that the system operator may initiate a TM recording while examining the substantially real time display. This feature completely obviates the difficulty inherent in the prior art, wherein the diagnostician was obliged to operate in partial or entire ignorance of the precise patient area for which he was preparing the said TM-mode recording.

The TM-mode operation further includes certain capabilities heretofore not provided in such instrument and especially, of course, not provided in the presence of the greatly augmented capabilities of the present system. Thus, and in addition to the capability of effecting a TM record with respect to the time-motion characteristics occuring along one or more of selected radial lines of the scan sector, the present system may be operated in an automatic mode—wherein successive TM scanning of each adjacent radial line is effected, in order to thereby obtain a TM recording of the entire sector under operator observation at the system display screen.

The present system further includes ECG input means, which enable ECG data from the patient to be directly provided to the said system. The ECG proper is displayed in real time on the system display screen, and means are further provided for enabling the generated ECG pattern to persist for a period sufficient to enable the operator to identify significant features thereof.

In accordance with a further aspect of the invention, an operator movable cursor (i.e. an indicia mark) is generated on the CRT screen, and may be positioned at a desired point on the ECG record. This operation serves a highly significant function during preparation of photographs. In particular, means are provided in the system which enable production of a photograph corresponding to the real time image at the point in the cardiac cycle identified by the cursor. This enables the operator to obtain a photographic readout at any precise point in the cardiac cycle which he may deem of pertinence to his examination.

In yet another aspect of the system, a keyboard input is associated with suitable alphanumeric character generator means, so as to enable insertion of alphanumeric and other information upon the visual display. Information may be thereby entered by the operator respecting such matters as patient identification, date of the examination, and other data of interest to the diagnostician or the institution effecting the patient testing. In addition, instrument parameters and related data is automatically displayed including data respecting the point of the ECG cycle of which the photograph is indicative. Information of the latter type may be correlated with the aforementioned cursor position which can also be provided to the display in the form of timing data specifying the time displacement from the R-wave or other significant datum in the ECG cycle.

A clock display may similarly be superimposed upon the display screen, as to provide a continual record— which can extend down to 1/100's of second, whereby each full frame (1/30 sec.) carries a distinct time identification. This type of information is significant for the aforementioned photographs, and is of special value in the course of interpreting the video recordings which can be secured by the present system.

The securing of the aforementioned categories of identifying and related data is deemed of significance, not only for normal record-keeping purposes, i.e., to enable ease of correlation of photographs and video recordings with patient records or so forth; but moreover, the said information is deemed significant in connection with medico-legal problems and/or for regulatory purposes, i.e., in order to conform to such requirements as may be imposed by the hospital or other institution utilizing the equipment or by state or federal agencies.

BRIEF DESCRIPTION OF DRAWINGS

The invention is diagrammatically illustrated by way of example in the drawings appended hereto in which:

FIG. 2 is a plan view, schematic in nature, of the display screen portion of the present apparatus;

FIG. 3 is an electrical schematic block diagram, illustrating operation of the system in a TM mode, as well as indicating certain aspects of the sector generation techniques;

FIGS. 4A, 4B and 4C are graphs, setting forth certain aspects of the sequence effected during making of photographs by the present system; and FIG. 5 is an electrical schematic block diagram illustrating the electronic persistance and exposure sequencing circuits shown as block 56 in FIG. 1.

DESCRIPTION OF PREFERRED EMBODIMENT

Figure 1:
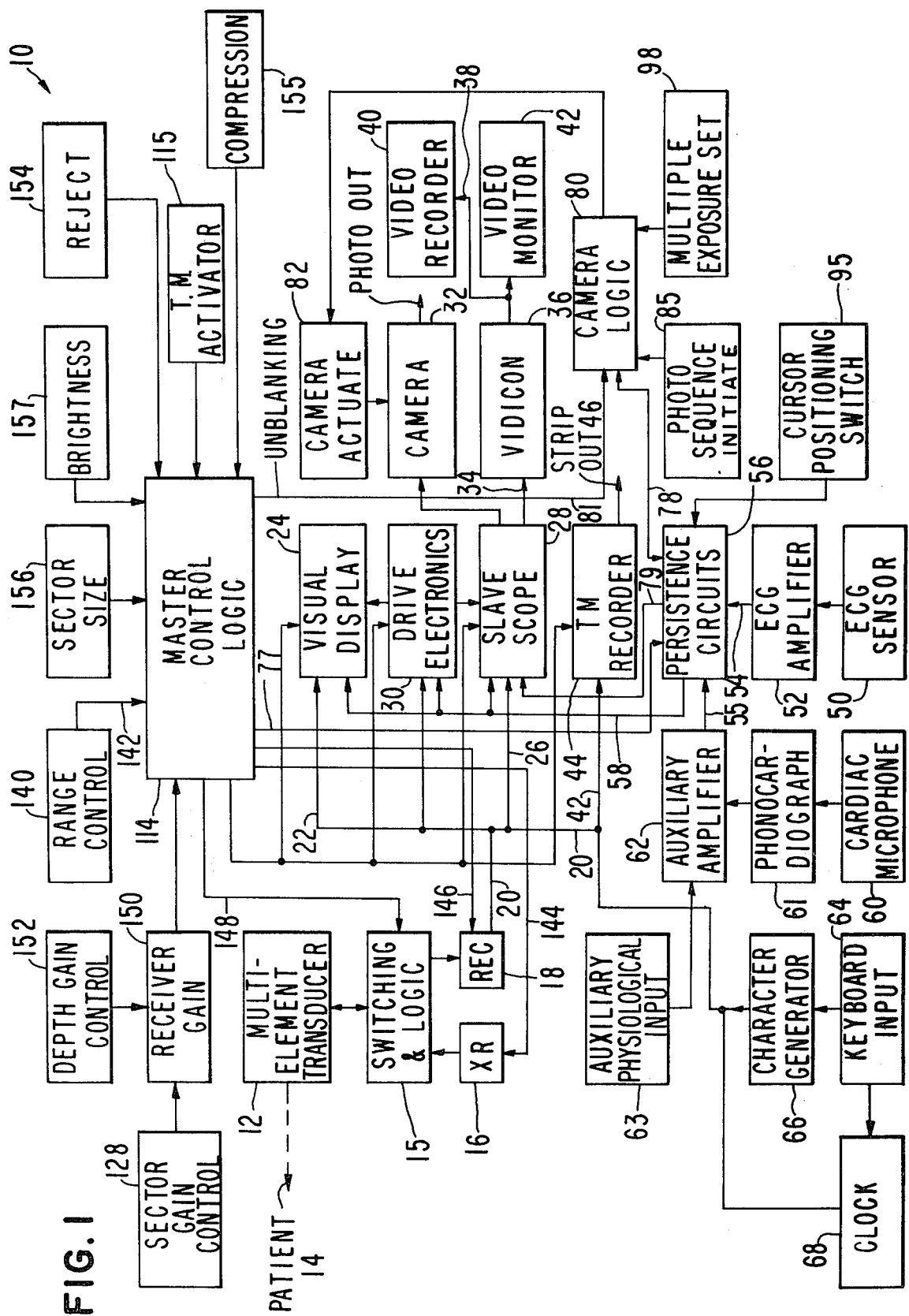
FIG. 1 is an electrical schematic diagram in block form and sets forth the key operative elements of a system in accordance with the present invention.

In FIG. 1 appended hereto, a display and recording system 10 is set forth in accordance with the present invention. System 10 operates upon ultrasonic principles and is intended primarily for use in effecting diagnosis of cardiac and cardiovascular conditions, although it will be evident to those skilled in the present art that the said system is useful in other diagnostic applications in that the system provides useful information in these further environments. However, because of its primary application to cardiac and cardiovascular diagnostics, the system applied to such an application will be emphasized in this specification.

The sonic transducer 12 utilized with system 10 is operatively associated with a patient 14, so as to enable the ultrasonic sound beam thereby produced to be projected into the regions of the heart and related structures. Thus transducer 12, as is known in the present art, can be positioned as to propagate its output between the ribs of the patient.

Although various transducer configurations as are known to be useful in conjunction with generation of two-dimensional images can be used with the invention including e.g. those based on so-called "near-field" linear arrays, transducer 12 preferably comprises a phased array consisting, for example, of a plurality of elements such as for example 32 piezoelectric elements arranged in a compact linear arrangement. In a typical instance, each such element may have a length of 12 mm, a width of 0.3 mm and center-to-center spacing between adjacent elements of 0.4 mm. Generally the transducer should be of a physical size to enable effective use in connection with a human, as for example propagation of ultrasound between ribs to enable display of the heart area. The thickness of the specific transducer elements utilized is determined by the operating frequencies, and can typically be of the order of 0.7 mm where a frequency of 2.5 MHz is utilized.

Transducer 12 is connected through switching and logic means 15 to a transmitter 16 and a receiver 18, and transmitted pulses at the desired ultrasonic frequency are phased by the timing sequence of the voltages applied to the individual transducer elements, as to steer the emitted sound beam in the desired direction. Adjustable delays are provided in each receiver channel, which enhance the reception from the same direction as the transmitted sound beam. By controlling the timing of the voltages applied to the transducer elements and the adjustable delays of the separate receiver channels, the beam is steered to desired angles of a fan-shaped sector. Operation of the steered array, the phasing, and the delay sequences, are effected so that a plurality of radial lines defining the said fan-shaped sector are successively generated with a relatively high number of such radial lines, typically in the range of 64 to 256, being utilized in the course of generating the entire sector. A set of such lines are generated over a short period, typically of the order of 1/30th of a second, whereby the corresponding display—(FIG. 2) on the system CRT display 24 is a high resolution, substantially real time image of the heart and related cardiovascular structures, the said visualization being in the so-called B-mode, i.e., one wherein tissue impedance variations are translated into brightness variations on the CRT screen.

Further details regarding the signal processing techniques utilized in connection with transducer 12 to generate the mentioned fan-shaped sector 25 (FIG. 2), are set forth in the copending application of William L. Beaver, Ser. No. 602,700, filed Aug. 7, 1975, and entitled "SIGNAL PROCESSOR FOR ULTRASONIC IMAGING", which application is assigned to the assignee of the present application.

The output from receiver 18 proceeding via line 20, is provided in parallel to three instrumentalities. Firstly, such output is provided via line 22 to a visual display 24, which as mentioned typically takes the form of a conventional CRT screen directly viewable by the system operator. It may however, comprise other display devices such as for example a plasma display panel. Via line 26, the said output is also provided to a slave scope 28. Slave scope 28 and display 24, are operated in synchronism by drive electronics 30, which if the CRT's are employed provides the required deflection voltages of each of the CRTs. In consequence of this arrangement, the precise display being provided at any given time for operator viewing at display 24, is also simultaneously present at slave scope 28.

Operatively associated with slave scope 28 is a reproductive means which may comprise a photographic camera 32 mounted in spaced relationship from the CRT screen of the slave scope as to enable direct photographing of such screen at selected times. An output image is also taken at 34 from slave scope 28 and provided to a conventional vidicon 36. The vidicon 36, in turn, provides an output 38 to a video recorder 40. A video monitor 42 may also be provided for monitoring the information being thus recorded. These last several elements and their mode of operation are well known in the art, and therefore further details of their functions and interconnections are not provided.

In accordance with a key aspect of the present invention, a third parallel output from receiver 18 is provided via line 42 to a TM recorder 44. TM recorders are per se well-known to those familiar with the art of cardiac diagnosis. In the usual application of these devices in echo cardiography, the sound modifying characteristics existing along a linear direction of structural examination are recorded on a strip output 46 as the said strip advances with time. In this sort of arrangement, the resultant pattern is thus indicative of the displacement with time of the structural features being observed by the echoing techniques. The TM recorder 44 used in the present system is of this same type; and while the manner in which it interacts with the remaining elements of the system 10 produce new and highly unexpected results (as will be hereinbelow discussed), the recorder per se may be of a conventional design. Thus, a recorder Model 1856 from Honeywell may be utilized in the present system, as may several other devices of this type as are known in the art.

Nextly, there is seen to be associated with system 10 an ECG sensing and recording means. In particular, an ECG sensor 50 is provided, which may constitute the usual electrodes and related paraphernalia operatively associatable with the patient being examined. The output from sensor 50 is provided to an ECG amplifier 52. In accordance with this aspect of the invention, the output 54 of ECG amplifier 52, after being processed by electronic persistence circuits of block 56, is provided via line 58 to visual display 24, as well as to slave scope 28. It will be appreciated that the ECG trace, as same develops on the CRT screen of display 24, will be generated in real time and would in principle therefore, only be visible as a point of light progressing across the screen. In order to render the trace useful for operator analysis, it is necessary to effect persistence of the developing trace for at least a portion of the ECG cycle sufficient to enable operator analysis. The electronic persistence circuits of block 56 are provided to effect such result. Apparatus for providing this feature is indicated in FIG. 5 and is described more fully below. Essentially the persistence function purpose is to refresh a portion of the ECG trace for a desired period. In a typical instance, for example, and referring to FIG. 2 the point 103 may be assumed to represent the developing point of the trace, i.e., the point being generated in real time on the CRT screen 102. The portion of the trace indicated at 101 may, however, be rendered persistent by the circuit of block 56, so that this portion of the developing trace remains visible for examination by the operator.

In accordance with an additional aspect of the invention, it may also be found useful to provide, in addition the the ECG input, a phonocardiograph capability or other physiological detecting and recording devices. Thus, a microphone 60 is provided, the input of which is connected to a phonocardiograph 61 and thence via auxilliary amplifier 62 to the same electronic persistance circuits of block 56 as are used for the ECG system, so that the phonocardiograph output can, if desired, be placed upon visual display 24 and recorded, photographed or so forth, by the various recording elements of the system. In similar fashion, other physiological inputs as indicated by auxiliary physiological input block 63 may be amplified by amplifier 62 and provided to circuits of block 56. Thus for example, the auxiliary input 63 may comprise a respiration monitor.

An operator actuated keyboard input 64 is provided in the present system, which enables insertion onto the various displays of identification data and of additional important information. In particular, the keyboard actuates an alphanumeric character generator 66 and/or a clock 68, which provide time data and various alphanumeric identification data through the lines 70 and 20 to the visual display 24 and slave scope 28. By referring to FIG. 2, it may thus be seen that certain information of the type just discussed may be inserted by the operator upon the display. For example, patient identification data by number, name, or so forth, appears at 104 and operator identification appears at 105, the date of examination at 106, and time information at 107, and camera sequence information at 109. The data at 111 comprises the elapsed time from the R-wave peak of the ECG to the time the camera effects a picture of the B-scan data as explained more fully below.

The types of information indicated serve several important purposes. In the simplest instance, the identification data, as it will appear on photographs and video recordings obtained by the present system, enables direct identification of the records to the patient, avoiding any possibility of error. The time information has indispensible significance in connection with the video recordings effected by video recorder 40. The time information in particular, as it is normally provided in 100ths of a second, uniquely identifies each frame on the CRT (i.e., each frame persists for 1/30th of a second). Hence, study of the video recording together with the time information, can enable precision determination of the motion characteristics of the structures depicted.

It should also be noted as significant, that the various data just mentioned are deemed to be of ever-increasing importance from a medico-legal and regulatory agency viewpoint. Thus, in many instances, hospitals and similar institutions, by virtue of their own internal regulations or requirements imposed upon them by insurance companies or so forth, require or at least desire, accurate data of the type mentioned, for use in possible legal proceedings based upon diagnosis; and similarly, state and/or federal regulatory agencies are increasingly placing stringent requirements upon the identification data associated with medical records.

The camera means 32 associated with the present system may be of any conventional construction. Various models of the well-known "Polaroid" cameras as well as display type xerographic cameras, as for example commercially available from Varian Associates are well suited for the present purposes. In accordance with the techniques utilized in the present system to enable photographs of displays at slave scope 28, camera logic 80 is provided which includes suitable logic circuitry for activating camera actuator 82, which, by electromechanical or similar means, effects tripping or triggering of the camera 32 to effect an exposure at a desired time. The operator selects the point in the ECG display at which the photographic exposure is to be effected, with the aid of camera logic 80 and electronic persistance and exposure sequence circuits 56. The latter in particular, acting through cursor positioning switch 95, moves a cursor mark to any preselected region of the ECG display 101, such cursor indication being for example a brightening of the ECG display at the desired point. Such a point is indicated in FIG. 2 by point 108.

The timing of the camera sequence is explained with the aid of FIGS. 4A through 4C. When a photograph is desired, camera logic 80 is activated by the operator initiating the photo sequencer 85. After activation, indicated at time 83 on the ECG 100 of FIG. 4A, camera logic 80 immediately blanks the screen of the slave scope by receiving the unblanking signal on line 81 from Master Control logic 114 and preventing it from being applied via cables 78 and 79 to slave scope 28. The blanked and unblanked condition of slave scope 28 is depicted in FIG. 48. The camera logic 80 through camera actuate 82 opens the shutter of camera 32 as depicted in FIG. 4C. The system then continues to operate with the slave scope screen blanked until the next R-wave (FIG. 4A) is detected by electronic persistant and exposure sequence circuit 56. When the horizontal position of the ECG arrives at the cursor marker 108 at time 89, a trigger signal is sent from circuits 56 to slave scope 28, to unblank the B-scan to provide one frame of cardiac data on slave scope 28. This unblanking period lasts about 20 milliseconds which is adequate to display and record one frame of B-scan data.

The slave scope 28 is then again blanked (at 93 in FIG. 48) until approximately one second later (at 97) when another unblanking occurs; but this time only the ECG signal on slave scope 28 is unblanked so that this information is then presented to the camera. The system is then blanked again (at 99) and the camera shutter closes, after which the display is again unblanked and normal operations are continued. The camera film is then advanced and the system is ready for another picture or for continued normal operations.

It will be further noted that a multiple exposure set means 98 is provided which can be set by the operator as to enable repeated exposures on the same photographic frame of the selected portion of the cardiac cycle. This may be desired in particular instances in order to obtain sufficient exposure or contrast in the photographic film or plate.

FIG. 5 is a block diagram of the electronic persistence and exposure sequence circuits 56 of FIG. 1. These circuits enable a persistant ECG signal to be displayed on the main display and slave scope 28 and provides signals with the aid of camera logic 80 to enable a photograph to be obtained at a predetermined point in the cardiac cycle.

ECG signals from the ECG amplifier 52 and phonocardiogram signals from amplifier 62 are coupled via lines 54 and 55 respectively to the amplifier 552 for amplifications to a level suitable for digitization, typically in the voltage range of 100 to 1000 millivolts. These signals are then digitized by the analog-to-digital converter 554 and fed into the random access memory 556. The address of memory 556 is determined either by the display counter 558 or by acquisition counter 560. Duplexer 562 selects which counter is coupled to the memory 556. During the acquisition phase of the ECG signal, duplexer 562 provides coupling only from the acquisition counter 560 to control the address of memory 556. The address of counter 558 is derived directly from clock 564 and the address of counter 560 is derived by dividing the frequency of clock 564 by divider 566. In a typical example, clock 564 may run at a frequency of approximately 51 kHz and divider 566 may typically divide this frequency by 256 leading to a frequency of approximately 200 Hz as the input frequency to counter 560. Counter 560 will continue to advance as it receives pulses from divider 566 until the counter is filled, that is until a most significant bit output is obtained on line 568. An output on line 568 resets flip-flop 570 so that the enable signal on line 572 is set to zero thereby halting further counts on counter 560. Counter 560 maintains this state until the next R-wave is detected by peak detector 574. When an R-wave is present, peak detector 572 applies a voltage on line 576 to AND gate 578. If counter 560 is full a most significant bit is present on line 568 and flip-flop 570 maintains a positive signal on the Q output 580. The combination of this positive output on 580 and the positive detector output from peak detector 574 activates AND gate 578 to produce a positive output on 582 which is applied to the reset input of counter 560 and the set input of flip-flop 570. Acquisition counter 560 then advances as it receives pulses from divider 566. By the above-described means the address of random access memory 556 is set to its lowest address at the peak of the R-wave, and subsequent memory locations are used to store the digital ECG signal as it is presented to memory 556 by ADC 554. Typically memory 556 may contain 512 memory locations so that approximately 2 full seconds of ECG information would be stored within memory 556.

So far the description of FIG. 5 has been directed toward how information from the ECG sensor is digitized and stored in memory 556. The reading of the ECG data from memory 556 and displaying it upon the output displays will now be described. The visual display 24 and slave scope 28 of FIG. 1 are capable of writing only one piece of data at a time on the display screen so that while the ultrasonic B-scan image data is being displayed upon the screen, no ECG information is presented to the display and slave scopes. It is only between successive frames of the B-scan picture that the ECG signal is presented to the display. Since it takes approximately 20 ms to display one frame of B-scanned information and successive B scans occur at 33-millisecond intervals, one has approximately 13 milliseconds between successive B scans to display the ECG information and alphanumeric information upon the screen.

Just after a B-scan has been completed, a control signal is supplied by the master control logic 114 of FIG. 1 to the persistence and exposure sequencing circuits FIG. 5 via control line 77. This signal hereafter identified as frame overhead indicates that the B-scan has been completed and that the displays are now ready to receive the ECG data from the persistence circuits. This control signal via line 77 simultaneously sets the memory 556 to the read mode permitting the stored ECG data to flow from memory 556 through the digital-to-analog converter 586 with output line 588 to the drive electronics 30 of FIG. 1 to provide the Y axis deflection signal for the display and slave scopes. The frame overhead signal on 77 also switches duplexer 562 to couple the address of display counter 559 to memory 556. The frame overhead signal on line 77 also resets the display cunter 558 so that the initial output address from display counter 558 corresponds to the first memory location in memory 556. As clock 564 is advancing counter 558 at approximately a 50 kHz rate, all 512 addresses in memory 556 will be read out in approximately a 10-millisecond period. The digital-to-analog converter 590 also receives the address from display counter 558 and converts it to an analog signal on line 592 that is coupled to drive electronics 30 of FIG. 1 to drive the X axis of the visual display and slave scope.

In order not to display ECG data from previous cardiac cycles that may remain in the upper part of memory 556, an unblanking signal is applied to the display scope when the count of display counter 556 is less than the count at acquisition counter 560. The unblanking signal is derived by applying the output signal on line 596 of digital comparator 594 with the frame overhead signal on line 77 in AND circuit 598 to produce the ECG unblank signal on line 599. Line 599 is coupled through cable 58 to visual display 24 of FIG. 1. Digital comparator 594 produces output on line 596 only when the count of display counter 558 is less than the count of acquisition counter 560. The unblanking signal which appears on line 599 ensures that only that part of the ECG will appear on the display screen that corresponds to the ECG in the current cardiac cycle and the point at the right-hand edge corresponds to the current time in the ECG cycle. Early in time after an R-wave peak has been detected, the trace visible on the screen is thereby very short and as time progresses this trace becomes longer and longer until it fills the entire screen.

The mechanism to provide a cursor indicator upon the displayed ECG signal and its use in controlling the camera sequence will now be considered. The use of the cursor positioning switch 95 has been indicated above in the description of FIG. 1. Up-down counter 612 is used to indicate the position of the cursor. The address in counter 612 can either be advanced in the forward direction or in the reverse direction by means of cursor positioning switch 95. By grounding terminal 616, by means of switch 614 the counter will advance whereas grounding terminal 618 will cause the counter to advance in the reverse direction as it is driven by clock 620. When the switch 95 remains in its center position the contents of up-down counter 612 will remain unchanged even though it is coupled to clock 620. The contents of counter up-down 612 is compared with the contents of display counter 558 by comparator 622. When the count in counters 612 and 558 are equal comparator 622 will put a signal on line 624 which is coupled to visual display 24 and slave scope 28 through cable 58 (FIG. 1). The ECG signals of both the visual display and slave scope are brightened, the displayed ECG signals for that one address thereby providing a cursor indication of that point in the cardiac cycle. By means of switch 95 the operator can place the cursor marker at any desired point in the cardiac cycle.

One of the main purposes of the cursor marker just described is to select and indicate the pre-selected point in the cardiac cycle at which the operator desires a photograph of the B-mode scan. The general sequence for camera operation is already described above. The operator, by switch means 95, places the cursor mark at the point in the cardiac cycle at which a photograph of the B-scan is desired. The photo sequence initiator 85 (FIG. 1), when activated by the operator, causes camera logic 80 to blank the screen of the slave scope by removal of the photo B-scan unblank signal on line 630 (FIG. 5) and opens the camera shutter as depicted in FIGS. 4B and C respectively. The time at which the screen is unblanked is selected to be the time at which the ECG signal arrives at point 108 of FIG. 4A. Referring now again to FIG. 5, this time occurs when the count of acquisition counter 560 is equal to the count in up-down counter 612. These two counts are compared by comparator 623 so that when these two counts are identical an output occurs on line 625. The signal on line 625 then unblanks the display for one frame and thereby exposes the camera film to the selected B-scan frame. The B-scan unblanking signal on line 626 is obtained from the output of logical OR 628. The inputs of logical OR 628 are the digital comparator output signal on line 625 and the proto B-scan unblanking signal on 630 which was derived in camera logic 80 of FIG. 1. During the camera sequence, the proto B-scan unblanking signal on 630 is zero so that an unblanking signal on 626 is obtained only if one is present on line 625. Line 626 is coupled through cable 58 (FIG. 1) to slave scope 28.

The circuits of FIG. 5 put out a logic signal to the camera control logic 80 via cable 78 on line 632. The purpose of this output signal is to indicate to the camera controller that the ECG has finished its sweep and therefore another exposure can be taken if so indicated by multiple exposure set 98 or if finished a single complete ECG signal can now be displayed via lines 588 and 592 permitting a full ECG signal to appear on the final film. Once this has been accomplished, the shutter can be closed and the frame will be complete.

System 10, when utilized for providing a TM recording may be utilized in one of two modes, each of which uniquely interact with the other elements of the present system. In particular, a unique advantage derived from the present system arise by virtue of the fact that the operator thereof is able to visually observe the two-dimensional real time image provided upon visual display 24 at the same time he initiates preparation and generation of a TM recording. As has already been pointed out, the prior art approaches to the production of TM recordings were either made from near-field arrays which do not produce a TM recording in the accepted format or were basically deficient in requiring the diagnostician to effect a TM recording without the benefit of certainty regarding precisely what structure was being investigated. In essence, only after such TM recording was obtained, could the investigator actually be apprised to that which he was investigating. In the present device the operator is able to select specific planes of interest for effecting a TM scan and, moreover, to select specific areas of the scan sector for which the TM recording is to be carried out, the instrument automatically angulating the probing ultrasonic beam. While the TM recording is being made, the operator may simultaneously observe the B-scan display to ensure the desired structures are being recorded. Another feature of the present system is that the particular section Being recorded on the TM recorder may be identified on B-scan display by an increase in brightness of the corresponding part of the image.

Referring to FIG. 3 (and also cross-referencing FIG. 2), a schematic block diagram appears setting forth details of the TM recording modes of operation. The CRT screen image is generally indicated at 110, such image being provided at visual display 34. As image 110 is an real time, the diagnostician can readily angulate or position transducer 12 to obtain the desired structures within the two-dimensional image. The image, as already discussed, is comprised of a series of radial lines 112, each line representing a preselected direction of the ultrasonic beam and the receiver steering pattern.

The schematic arrangement of FIG. 3 provides a switching and control subsystem which will select one or a series of predetermined lines from the raster of radial lines 112, and present the selected line (or in sequence the lines) to the TM strip chart recorder 44 for TM scan. The lines for the TM scan may be selectively swept through a part or all of the entire range of the raster set occuring in the B-scan picture.

In addition to functions described in connection with FIG. 1, master control logic 114 provides inputs to address the TM register 116 (FIG. 3), and to address the B register 118 and further, increments each said address register. TM address register 116 contains the address of the radial scan line presented on TM recorder 44, and the B address register 118 contains the address of the current radial line 112 displayed on visual display 34. Logic 114 also provides control through line 120 to duplexer 122 and electronic switch 126 so that when TM address register 116 is coupled to beam angle address register 125, electronic switch 126 couples the video output on line 132 to TM recorder 44. When B address register 118 is coupled to the beam angle address register 125, the video output line 132 is coupled only to visual display 34.

In operation of system 10 for generation of the B-mode image 110, duplexer 122 maintains the coupling of B address register to the beam angle address register and the video output is coupled only to visual display 34. In this mode, control logic 114 increments the address contained in register 118 by one number for each radial line that is scanned, until all of the lines of the selected sector have been swept completely to generate one frame on the CRT display. It will then go back to the initial address and repeat the same process for succeeding frames. Thus, in this mode of operation, the diagnostician can orient transducer 12 to obtain the desired cross-sectional plane for which he wished to obtain his TM-mode scan. In all instances the transducers outputs are controlled and processed by transmitter/receiver, and switching logic block 127, are controlled by beam angle address register 125 (corresponding to elements 15, 16 and 18 in FIG. 1), and then by detector and video amplifier means 129, to enable the said visual display.

When the diagnostician is ready for the said TM scan, he activates T.M. activator means 115 (FIG. 1) for controlling logic 114 which then modifies the operation. In particular, both address registers 116 and 118 are initialized to an address representing a scan line at the edge of the sector. Via manual set control 117 the address of a single TM-line sought to be examined may be set into register 116; or logic 114 may be set to effect TM recording of a selected angle within the scan sector; i.e. an angle in image 110 comprising a given number of radial lines 112. Duplexer 122 is then set to transfer the address of TM address register 116 to address register 125 for the beam angle. A signal from control logic 114 via cable 130 then initiates the scan line. The video output at line 132 from detector and video amplifier means 129 contains the signals produced by any reflections occuring along this line, and indications of such reflections are shown by intensity modulations of the corresponding scan line produced at the strip chart recorder 44 and upon visual display 34. Control logic 114 then switches duplexer 122 to transfer the address of B address register 118 to address register 125 of the sector scanner system. Again, a signal via cable 130 originating at logic 114, activates block 127 and one line of information appears in the video output line 132—which is then coupled only to the visual display 34.

The address in register 125 is also coupled to the CRT display 34 via cable 124 to activate a corresponding radial line 112 in this display, and a timing signal from logic 114 via cable 130 initiates the writing of this radial line. The B-register 118 address is then incremented by one unit and duplexer 122 is switched back into the TM register and a further scan line is thereafter produced on strip chart recorder 44. On completion of this scan line, duplexer 22 is switched back to the B-register and a new scan line on the CRT of display 34 is generated and the B-register again incremented by one unit. This process is continued until the B-register 118 has been incremented through the totality of addresses for the particular sector angle that has been selected. Upon completion of the last scan line of the last address in B register 118, duplexer 122 is returned to the TM register. If the system has been set to effect a TM scan through a selected angle, then the address of TM register 116 is advanced by one increment, and this whole process is reinitiated and repeated through the next CRT frame. After repeating the cycle for the number of frames equal to the totality of lines in the selected angle to be recorded by the TM recorder, the address of the A register 116 will have been incremented through the entire selected angle and correspondingly, a complete TM recording will have been made on the strip chart recorder 44, corresponding to the entire portion of the real-time picture displayed upon CRT display 34 which is included within the selected angle. During the entire process of producing the TM scan, the operator is able to maintain on the visual display 34 the structures within the entire scanned region. In addition, the radial line that is being recorded on TM recorder 44 is displayed as a brightened radial line on the visual display since this line is displayed at a higher repetition rate than the other lines on the visual display.

It might be pointed out here that the indicator marks 113 of FIG. 3 comprise a series of marks spaced at intervals corresponding to one centimeter distances within the human body. These indicator marks provide valuable assistance to the diagnostician in judging the size and spacing of structures being observed in the image 110. These indicator marks are generated in Master Control logic 114 (FIG. 1) and are displayed on both the visual display 24 and slave scope 28 during the frame overhead interval between B-scans. They are thus preserved by the photographic record made by camera 32 or video record made by video recorder 40. Since the size of the image may vary depending upon the enlargement of the photographic or video display image, it is important to have suitable calibrations that relate the final image to the actual size of the original structures. Sector size control 156 may also be used to change the size of the displayed image, however master control logic 114 takes this size information into account and provides the appropriate scaling of indicator marks 113.

As a further aspect of the present invention, the real time two-dimensional displayed image and thereby the resultant derivative readouts may, by means of the present system, be subjected to a variety of image manipulation procedures, which enable such useful results as varying the resolution of the image, or enabling the operator to focus his attention on certain specified portions of the image, or so forth. Continuing, therefore, to refer to FIG. 1, master control logic 114 provides control input signals to drive electronics 30, and to transmitter 16 and receiver 18 associated with transducer 12.

An input to master control 114 is also provided from a receiver gain control 150 which, in turn, is influenced by operator adjustment of depth gain control 152. Depth gain control 152 enables the operator to adjust the receiver gains so as to increase such gain only where the receiver is processing specified portions of the sector scan image 110. The net result of this arrangement for operator viewing, is that such operator can adjust the system so as to intensify lower portions of the image or upper poritons, or selected regions of the upper or lower portions. By means of sector gain control 128, the operator can also adjust the system so as to adjust the gain of pre-selected angular regions of the sector so as to highlight the desired structures being imaged. Such angular gain adjustment also enables the operator to compensate for reduced sensitivity of the transducer to detect signals obtained at large scan angles. By proper adjustment of sector gain control 128 a uniform image may be obtained even at very large sector angles.

The master control logic 114 is similarly provided with inputs from reject control 154 and from data compression control 155. Reject control 154 acts to establish a threshold level for rejection of signals at receiver 18, i.e., to thereby enable noise rejection, as is known in the art of receiver operation. The compression control 155 varies the receiver gain characteristics so as to enable non-linear processing, i.e., so that the output from the receiver proceeding toward the display can be rendered proportional to the log of the input, thereby enabling expansion of scale in an area of maximum signal interest. Techniques of this sort are again well-known per se in the signal processing arts.

In addition to the foregoing controls, which are directed at image manipulation, two further controls useful in system 10 are provided. These are a brightness control 157, which essentially functions to increase and decrease the overall image display brightness by applying, in accordance with its setting, an appropriate DC bias to the grid of the CRT in the several displays and, in addition, a sector size control 156 is provided, which enables the operator at his selection to vary the angle of the sector appearing in the scan. Thus, in a typical instance, the angle being examined may be varied among such settings as 20, 40, 60, and 80 degrees. In accordance with this aspect of the invention, the sector size control 156, acting through master control 114, functions to select a set of radial raster lines 112, the group of lines selected serving to define the sector angle set. It should be appreciated in this connection that a relatively high number of such radial lines are utilized to define the sector scan in the present system. As already mentioned, 64 such lines may typically be present when a maximum range of 21 cm has been selected. Regardless of the sector size set within the system, when the system is set to its maximum range of 21 cm the total number of such lines will remain the same. (It is noted that any maximum range may be selected. 21 cm represents a normal maximum to image human organs.) Thus, it will be evident that the total number of available radial lines is considerably greater than the 64 mentioned. In fact, in a typical arrangement, 256 such lines are available to the system; but a total of 64 such lines will be selected from the overall possible number of 256, in accordance with the setting on sector size control 256. The group selected defines the particular sector and is sequentially furnished to address register 125 as shown in FIG. 3, to enable generation of the sector scan. The correllary of the operation just described is, of course, that the definition achieved within the narrower sector scans will be greater than that of the broader scans in that the total number of raster lines remains the same. Accordingly, this feature of the invention enables the operator to achieve increased definition of the image by reducing the angle of the sector scan after initially locating the region of interest to him, whereby greater structural details become evident in the displayed image, as well as in the recordings that may be effected by system 10 in correspondence to the displayed image.

As one aspect of the image manipulating features of system 10, a range control 140 is provided, which is connected to master control 114 through line 142. Range control 140 includes adjustable elements enabling the system operator to vary the maximum range or depth of the sector scan so as to adapt the system for use with patients having different physical attributes, for example, the range control may be adjusted to enable viewing at depths up to 21 cm from the transducer or at 7 or 14 cm. The more limited depths are particularly appropriate where the cardiovascular structures of an infant are to be examined. Range control 140 operating through master control 114, which, as indicated, controls the transmitter 16, receiver 18 and switching and logic means 15 through control cables 144, 146, and 148, enables such result by varying the trigger pulse rate to the elements of the transducer.

The range control permits a greater number of radial lines to be used while examining structures at shallower depths. In the examples above 64 lines were typically used for examining structures up to 21 cm deep. By restricting the depth to 14 or 7 cm a total of 96 or 192 lines respectively are used. The greater line density obtained with the restricted depths permits greater structural details to become evident in the displayed images.

While the present invention has been particularly set forth in terms of specific embodiments thereof, it will be understood in view of the present teaching that numerous variations upon the invention are now enabled to those skilled in the art, which variations yet reside within the scope of the present teaching. Accordingly, the invention is to be broadly construed and limited only by the scope and spirit of the claims now appended hereto.

We claim:

1. An ultrasonic system of the type utilized in patient cardio and cardiovascular diagnosis comprising:

first means including a multi-element transducer for generating and displaying a fan shaped two-dimensional real-time operator-viewable image of a patient region being examined from ultrasonic energy directed into said patient by said transducer and reflected out of said region into said transducer, whereby said two dimensional real-time image is generated by said first means;

ECG recording means operatively associated with said first means, and adapted for connection to said patient being examined, for generating an ECG output from said patient;

means for displaying in real time said ECG output simultaneously with said fan shaped two-dimensional operator viewable image of said patient region being examined on an operator viewable display; and means responsive to said means for generating said image, for effecting simultaneously with said fan shaped real time two-dimensional image and said ECG output, a TM recording corresponding to a preselected region of said fan shaped real time two-dimensional image viewable during patient examination.

2. A system in accordance with claim 1 further comprising means for refreshing at least a portion of said ECG output on said operator viewable display, thereby enabling persistence of said ECG output for study by said operator.

3. An ultrasonic system of the type utilized in patient cardiac and cardiovascular diagnosis comprising:

first means including a multi-element transducer for generating and displaying on an operator-viewable display a fan shaped two-dimensional real-time operator viewable image of a patient region being examined, said transducer directing ultrasonic energy into said patient and receiving ultrasonic energy reflected out of said region whereby said two-dimensional real-time image is generated by said first means;

ECG recording means operatively associated with said first means, and being connected to said patient being examined for generating an ECG output from said patient, said ECG recording means including second means for displaying in real time said ECG output of said patient being examined on said operator-viewable display whereby said ECG output is simultaneously displayed with said two-dimensional real-time image on said operator-viewable display;

a slave display for displaying a second image corresponding to the ECG output and two-dimensional real-time image being displayed on said operator viewable display, said slave display being synchronized with said operator-viewable display;

control means coupled to said slave display for controlling said second image on said slave display; and camera means coupled to said control means and said slave means for photographing said second image on said slave display, whereby photographs of the second image may be produced at selected points in the display of said ECG output in response to said control means.

4. A system in accordance with claim 3 in which said control means includes means for sequentially blanking and unblanking said second image on said slave display for predetermined periods, and means for actuating said camera means to effect a photographic exposure of said second image during the unblanking period.

5. A system in accordance with claim 4, including means for coordinating said unblanking period with a predetermined location on the displayed ECG output, whereby said photographic exposure may be effected at a preselected point of said display of said ECG output.

6. A system in accordance with claim 5, including means for generating on said operator-viewable display a cursor positionable at a preselected point on the ECG output; and means for effecting said unblanking and actuating of said camera means at said preselected point marked by said cursor on the real-time display of said ECG output of a patient being examined.

7. A system in accordance with claim 6, wherein said operator-viewable display comprises a CRT having a CRT beam; and wherein said means for generating said cursor comprises means for establishing addresses for said cursor display, an operator-actuated up/down counter for setting values corresponding to cursor display addresses, display counter means having an output indicative of said CRT beam position during said ECG output display, and comparator means for generating a brightening signal for enabling visualization of said CRT beam positions when the output of said display counter means is at an address for the cursor display corresponding to said value set in the up/down counter means by said operator.

8. A system in accordance with claim 7, wherein said means for coordinating said unblanking comprises means for normally blanking said display, detector means responsive to occurrence of the R-wave in said ECG output, acquisition counter means actuated by said detected R-wave for establishing addresses of preselected points of said ECG output, and second comparator means for providing a second output enabling said unblanking upon said counter means indicating an address corresponding to the value set in said up/down counter.

9. An ultrasonic system of the type utilized in patient cardiac and cardiovascular diagnosis comprising:
   first means including a multi-element transducer for generating and displaying a fan shaped two-dimensional real-time operator-viewable image on an operator-viewable display of a patient region being examined from ultrasonic energy directed into said patient by said transducer and reflected out of said region into said transducer, whereby said two-dimensional real time image is generated by said first means;
   ECG recording means operatively associated with said first means, and being connected to said patient being examined, for generating an ECG output from said patient, said ECG recording means comprising means for displaying said ECG output as a real-time ECG trace on said operator-viewable display for a patient being examined and means for refreshing at least a portion of said ECG output on said operator-viewable display thereby enabling persistence of said ECG output for study by said operator.

10. A system in accordance with claim 9, wherein said ECG refreshing means comprises means for digitizing said ECG output to provide digitized values of said ECG output memory means for storing the digitized values; means for reading out the stored values from said storage addresses in said memory means; and means for coverting the read-out values whereby said ECG output is generated on said operator-viewable display means.

11. A system in accordance with claim 10, including means for correlating the storage addresses of said stored values and the read-out thereof with the occurrence of an R-wave in said ECG output.

12. A system in accordance with claim 10, wherein said operator-viewable display comprises a CRT.

13. An ultrasonic display and recording system of the type utilized in diagnostic medicine, comprising: first means for creating a two-dimensional real-time display image on an operator-viewable display of a region of the patient being examined from ultrasonic energy propagated into and received back into said first means from said region; video recorder means coupled to said first means for recording said two-dimensional real-time display image over an extended interval thereby creating a recorded video image; ECG recording means coupled to said operator viewable display operatively associated with said first means for generating an ECG output from said patient and for simultaneously displaying said ECG output in real-time with said two-dimensional real-time display of said patient region on said operator viewable display; means for generating image time data coupled to said operator viewable display; and means for simultaneously superimposing on said display said image time data, whereby said recorded video image may be analyzed with respect to changes in said region bing examined as a function of time.

14. A system in accordance with claim 13, further including TM recording means for simultaneously effecting a TM recording of said two-dimensional real-time display image with the displaying of said two-dimensional real-time image.

15. An ultrasonic display and recording system of the type utilized in diagnostic medicine, comprising: first means for creating a two-dimensional real-time display image on an operator viewable display of a region of the patient being examined from ultrasonic energy projcted into and received back into said means from said region; ECG recording means coupled to said operator viewable display and operatively associated with said first means said ECG recording means adapted to be connected to a patient, including means for displaying the ECG output simultaneously with said two-dimensional real-time display image, said display means having an R-wave occurrence in real time of the patient being examined; on said operator viewable display; and means for rendering at least the portion of the ECG output extending from R-wave occurrence to the real time display persistently visible, thereby enabling study of said ECG output by said operator.

16. A system in accordance with claim 15, wherein said means for rendering said ECG output portion visible includes means for digitizing said ECG output, memory means for storing said digitized values as a data bit stream, means for reading out said data bit stream as a signal, thereby generating said ECG output portions on said operator-renewable display.

17. A system in accordance with claim 16, wherein said display means comprises a CRT.

* * * * *

REEXAMINATION CERTIFICATE (2257th)
United States Patent [19]
Anderson et al.

[11] B1 4,413,630
[45] Certificate Issued Apr. 5, 1994

[54] SECTOR SCANNER DISPLAY AND RECORDING SYSTEM FOR ULTRASONIC DIAGNOSIS

[75] Inventors: Weston A. Anderson; Lloyd D. Clark, both of Palo Alto; William L. Beaver, Los Altos Hills, all of Calif.

[73] Assignee: Diasonics Delaware, Inc.

Reexamination Request:
No. 90/002,716, May 4, 1992

Reexamination Certificate for:
Patent No.: 4,413,630
Issued: Nov. 8, 1983
Appl. No.: 239,251
Filed: Mar. 2, 1981

Related U.S. Application Data

[60] Division of Ser. No. 914,323, Jun. 12, 1978, Pat. No. 4,274,422, which is a continuation of Ser. No. 673,500, Apr. 5, 1976, abandoned.

[51] Int. Cl.$^5$ .............................................. A61B 8/00
[52] U.S. Cl. ................................ 128/660.04; 128/712
[58] Field of Search ...................... 128/660.04, 660.05, 128/661.01, 660.09, 661.03–661.1, 687–688, 696, 700, 712

[56] References Cited

U.S. PATENT DOCUMENTS

| | | |
|---|---|---|
| 3,451,260 | 6/1969 | Thurstone . |
| 3,541,848 | 11/1970 | Thurstone . |
| 3,605,724 | 9/1971 | Flaherty . |
| 3,777,740 | 12/1973 | Hokanson ..................... 128/661.09 |
| 3,786,476 | 1/1974 | Graves et al. . |
| 3,789,833 | 2/1974 | Bom . |
| 3,792,613 | 2/1974 | Couture . |
| 3,817,089 | 6/1974 | Eggleton et al. . |
| 3,827,115 | 8/1974 | Bom . |
| 3,830,223 | 8/1974 | Beretsky et al. . |
| 3,922,911 | 12/1975 | Groves et al. ................ 128/661.08 |
| 3,936,791 | 2/1976 | Kossoff . |

(List continued on next page.)

FOREIGN PATENT DOCUMENTS

| | | |
|---|---|---|
| 2013620 | 10/1970 | Fed. Rep. of Germany . |
| 2053669 | 5/1972 | Fed. Rep. of Germany . |
| 1573745 | 2/1974 | Fed. Rep. of Germany . |
| 2543678 | 4/1976 | Fed. Rep. of Germany . |
| 2544094 | 5/1976 | Fed. Rep. of Germany . |
| 2632562 | 10/1977 | Fed. Rep. of Germany . |

OTHER PUBLICATIONS

(Author Unknown), "Line Recorder for Echocardiographic Studies of the Heart", Bio-Med. Engrg. vol. 7, No. 3 (Apr. 1972) pp. 135–136.

Lowe, P. R. "The Application of Directly Heated Photothermographic Paper to Echocardiology", Jrnl. of Applied Photogr. Engrg (USA) vol. 7 No. 5, Oct. 1981.

Carpenter, D. A. et al "A Multi-Mode Real-Time Scanner", UTS in Med. & Biology, vol. 6, No. 3, pp. 279–284 (1980).

(List continued on next page.)

*Primary Examiner*—Francis Jaworski

[57] ABSTRACT

Improvements are disclosed in an ultrasonic display and recording system of the type utilized in diagnostic medicine with particular applicability in cardiovascular diagnosis. The system includes a multi-element transducer for generating and receiving ultrasonic energy which is propagated into and reflected back from the cardiovascular region of the patient being examined, and also includes means for generating a two-dimensional real time display and/or image of the zone of examination. TM recording means are associated with the system and may be actuated to effect a TM recording corresponding to a preselected region of the real time image being observed. An ECG output signal is also displayed in real time with the two-dimensional image, and photographs of the displays may be produced at selected points in the ECG cycle in accordance with a setting made by the system operator. The system includes provision for generating video recordings; and means for imposing various identification and time data upon the displays.

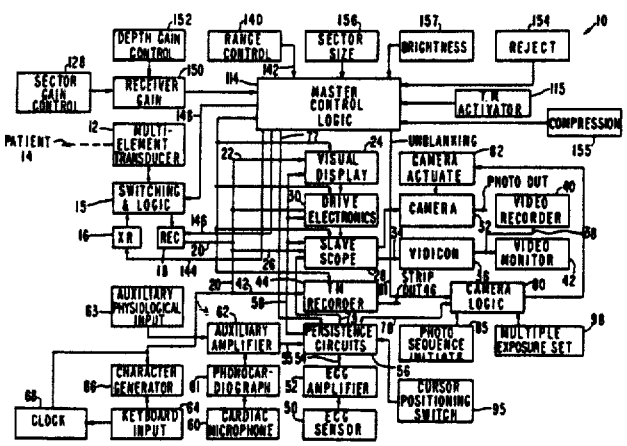

U.S. PATENT DOCUMENTS

| | | |
|---|---|---|
| 3,938,502 | 2/1976 | Bom |
| 3,954,098 | 5/1976 | Dick et al. |
| 3,995,259 | 11/1976 | Harris et al. |
| 4,010,634 | 3/1977 | Baumgartner |
| 4,100,916 | 7/1978 | King |
| 4,151,834 | 5/1979 | Sato et al. |
| 4,398,540 | 8/1983 | Takemura et al. ......... 128/661.09 X |
| 4,509,525 | 4/1985 | Seo ............................ 128/661.09 X |

OTHER PUBLICATIONS

Brondestini, M. "Topoflow—A Digital Full Range Doppler Velocity Meter", IEEE Trans. on Sonics & Ultrasonics, vol. SU-25 No. 5 (Sep. 1978) pp. 287-293.

Whittingham, T. A. "A Multiple Transducer System for Heart, Adbominal & Obstetric Scanning", Conf: Proc. of Zd Europ Congress UTS in Med, Munich 12-16 May 1975 pp. 59-66.

Barber, F. et al "Ultrasonic Duplex Echo–Doppler Scanner", IEEE Trans. BME vol. 21, No. 7, pp. 109-113 Mar. 1974.

Evans, T. C. et al "The Development of High Resolution UTS Imaging Technique for Detection & Assessment of CV Disease", NIIS Document PB-236-434 Aug. 1974.

Baker, D. W. "Pulsed Ultrasonic Blood-Flow Sensing", IEEE Transactions vol. SU-17, No. 3 Jul. 1970 pp. 170-184.

Eversden, I. D. "Detecting Introcranial Pressure Waves with Ultrasound", Ultrasonics Conf. Digest 3rd Intnl Conf. on Medical Physics Göteborg, Sweden (1972).

Donnerstein, R. et al "Digital Range–Coated Echocardiographic Tracking", Med. Instrumentation vol. 12 No. 3 May-Jun. 1978 pp. 184-188.

Emerson, R. et al "Maximal Instantaneous Mitral Valve Velocities Measured w/Dig. Echocardiographic Tracking System", IEEE BME Trans. vol. BME-24 No. 1, pp. 71-73 Jun. 1977.

Dr. Nicholas Bom et al., "Ultrasonic Viewer for Cross Sectional Analysis of Moving Cardiac Structures," *BioMedical Engineering*, Nov., 1971.

Dr. Nicholas Bom, *New Concepts in Echocardiography, 1972, pp. 9-98*.

Dr. Nicholas Bom et al., "An Ultrasonic Intracardiac Scanner," *Ultrasonics*, Mar, 1972, pp. 72-76.

von Ramm, "A Real Time Digitally Controlled Ultrasound Imaging System," Duke University Dissertation Thesis, 1973, 4 pages.

vor Ramm, Thurstone, "Thaumascan: Design Considerations and Performance Characteristics," vol. 1, *Ultrasound in Medicine*, pp. 373-378, 1974.

Correspondence from Laurie S. Hane of Morrison & Foerster to Ronald S. Wynn of Brobeck, Phleger & Harrison dated Nov. 20, 1992, pp. 1-4.

Williams, Smith, "Versatile Echoscanner," Abstract, AIUM Conference Booklet, Oct. 7-9, 1975.

Somer, "Application of a Non-Linear Processing Technique to Ultrasound Pulse-Echo Systems for Improving Angular Resolution" in *Proceedings of the Conference on Ultrasonics in Biology and Medicine* UBI-OMED-70, Jablonna-Warszaw, pp. 201-213, 1970.

Takemura, et al., "High Speed Ultrasono-Cardiotomography", BME74-10, pp. 19-29.

Sho 60-9290, "Japanese Patent Provisional Publication". 50–

Takemura, et al, "Simultaneous Display of High Speed Ultrasonocardiotomoghram and ECG" Speech Texts for the 28th Conference of Japan Ultrasound Diagnostic Association, pp. 51-52.

Sho-5064479 "Japanese Utility Model Provisional Publication".

C. R. Hill, "Medical Ultrasonics: An Historical Review", *British Journal of Radiology*, pp. 899-905 Oct., 1973.

D. McSherry, "Ultrasonic Cardiac Imaging and Image Enhancement Techniques", 1974 *IEEE Ultrasonics Symposium Proceedings*, pp. 5-11.

C. D. Watkins, G. E. Crossley, "A 9 GHz Phase Scanned Linear Array Antenna," *International Conference on Radar—Present and Future*, Oct. 1973, pp. 81-87.

R. Gramiak, R. C. Waag and W. Simon, "Cine Ultrasound Cardiology," vol. 107 *Radiology*, Apr. 1973, pp. 175-180.

R. C. Waag, R. Gramiak, "Computer-Controlled Two-Dimensional Cardiac Motion Imaging," 1974 *IEEE Ultrasonics Symposium Proceedings*, pp. 12-15, 1974.

R. C. Eggleton, et al., "Visualization of Cardiac Dy- (List continued on next page.)

OTHER PUBLICATIONS namics with Real Time B-Mode Ultrasonic Scanner", *Ultrasound in Medicine*, vol. 1, Proceedings of the 19th Annual Meeting of the American Institute of Ultrasound in Medicine, pp. 385-393.

R. C. Eggleton, et al., "Real Time Mechanical Scanning System Compared with Array Techniques", *IEEE Ultrasonic Symposium Proceedings*, pp. 16-18.

R. E. Daigle, et al. "A Duplex Scanning System for Pediatric Cardiology", *Ultrasound in Medicine*, vol. 3B, Engineering Aspects, pp. 1209-1211.

F. L. Thurstone and O. T. von Ramm, *A New Ultrasound Imaging Technique Employing Two-Dimensional Electronic Beam Steering*, Department of Biochemical Engineering, Duke University, Durham, North California 27706, pp. 249-259.

Fredrick L. Thurstone and Olaf T. von Ramm, *Acoustical Imaging with a Linear Phased Array*, 1975 Ultrasonic Symposium Proceedings, IEEE, Cat. #75 CHO 994-4SU, pp. 73-74.

F. L. Thurstone and O. T. von Ramm, *Electronic Control of B-Mode Scanning*, 1977 Ultrasound in Medicine, vol. 3B, Engineering Aspects, pp. 1807-1808.

T. W. Whittingham, "A Multiple Transducer System for Heart Abdominal and Obstetric Scanning", Ultrasonics in Medicine, 1975, pp. 60-66.

*Cardiac Ultrasound*, Edited by Raymond Gramiak, M. D. and Robert C. Waag, Ph.D., The C. V. Mosby Company, pp. 1-276.

M. Hussey, et al., "Ultrasonic B-Scanning of the Heart with an ECG Gated Television Display", *Ultrasonics*, Mar. 1973, pp. 73-76.

Gilbert D. Devey, et al., "Ultrasound in Medical Diagnosis" Sci Am, May, 1978, pp. 98-112.

H. Yokoi, et al., "Medical Application of a New Electro-Scanning Ultrasonic Diagnostic Equipment", *Ultrasound in Medicine*, vol. 3B, Engineering Aspects, pp. 1565-1572.

Yasuhiko Takemura, et al., "Highspeed Ultrasono-Cardiotomograph, Sonolayergraph Model SSL-51H", Toshiba Review, No. 98, Jul.-Aug., 1975, pp. 25-30.

Ronald E. Daigle, et al., "Esophagel Duplex Scanner", *Section VII F*, Exhibit 343-A, Sep. 9, 1992, pp. VIIF F-1- VIIF F-31.

K. Katakura, et al, "Electronic Sector Scanning System", *Ultrasound in Medicine*, vol. 3B, Engineeering Aspects, pp. 1805-806.

Reginald C. Eggleton, et al, "Real time B-Mode Mechanical Scanning System", *Application of Optical Instrumentation in Medicine III*, vol. 47, Aug. 1-2, 1974, pp. 96-100.

Donald W. Baker, et al., "Cardiac Blood Flow Detection", *Ultrasound in Medicine*, vol. 2 pp. 317-318.

Griffith, J. M. et al., "A Sector Scanner for Real Time Two-Dimensional Echocardiography, Circulation, vol. XLIX, Jun. 1974, pp. 1147-1152.

Kikuchi, Y. et al., "Ultrasono-Cardio-Tomography, Japan Electronic Engng., Oct. 1970, pp. 53-60.

Barnes, R. W. et al., Un Ultrasound Moving Target Indicator System for Diagnostic Use, IEEE BME Trans, vol. 18, No. 1, pp. 4-8, Jan. 1971.

Springer, John, "High-Speed Shift Registers Use TTL RAMs and Counters To Do All The Shifting", Electronic Design, vol. 18, pp. 146-148, Sep. 1973.

Theodore C. Cheston, et al, "Array Antennas", Radar Handbook, Chapter 11, pp. 11-1-13-1.

Lea and Fediger, "Echo Cardiography", Philadelphia, 1972, pp. 13 and 17-19.

Barber, F. E., et al., "Duplex Scanner II: For Simultaneous Imaging of Artery Tissues and Flow," *IEEE*, 1974 Ultrasonic Symposium Proceedings, pp. 744-748.

Yoshikawa, Y., et al. "Scanning Methods in an Electro-Scanning Ultrasonic Diagnostic Equipment", *Ultrasound in Medicine*, vol. 3B, pp. 1855-1856.

Erikson, Kenneth R., et al., "Ultrasound in Medicine—A Review," *IEEE Transactions on Sonics and Ultrasonics*, vol. SC-21, No. 3, pp. 144-170, Jul. 1974.

Kikuchi, Prof. Dr. Yoshimitsu, et al., "Ultrasono-Cardio-Tomography,"*Japan Electronic Engineering*, pp. 53-60, Oct. 1970.

von Ramm, O. T. et al., Acoustical Holography, vol. 6, pp. 91-102.

King, "Real time Cross sectional Ultrasonic Imaging of the Heart using a Linear Array Multi element Transducer", Journal of Clinical Ultrasound, vol. I, No. 3, pp. 196-200, 1973.

Thurston, et al., "A New Ultrasound Imaging Technique Employing Two Dimensional Electronic Beam (List continued on next page.)

OTHER PUBLICATIONS

Steering" Acoustical Holography, vol. 5, pp. 249-259, P. S. Green, editor, Plenum Press, 1974.

von Ramm, et al., "Cardiovascular Diagnosis with Real Time Ultrasound Imaging" Acoustical Holography, vol. 6, pp. 91-102, No. Booth, editor, Plenum Press, 1975.

von Ramm et al., "Conf. UTS In Medicine", vol. 1, pp. 373-378, Seattle, Wash., 1974.

von Ramm, "A Real Time Digitally Controlled Ultrasound Imaging System", 1973.

Conference agenda, 20th Annual Conference American Institute of Ultrasound in Medicine and 4th Annual Conference American Society of Ultrasound Technical Specialists, held Oct. 4-9, 1975, Benton Convention Center, Winston Salem, N.C., pp. 37.

J. C. Somer, Electronic Sector Scanning for Ultrasonic Diagnosis, *Ultrasonics,* 1968, pp. 153-159.

Kamphuisen, et al., Two-dimensional Echoencephalography with electronic sector scanning, *Journal of Neurology, Neurosurgery and Psychiatry,* 1972, pp. 912-918.

J. C. Somer, Electronic Sector Scanning in Cerebral Diagnosis, published in the *Proceedings of the Second World Congress on Ultrasonics in Medicine,* Jun., 1973, pp. 304-308.

Somer et al., "Ultrasonic Tomographic Imaging of the Brain with an Electronic Sector Scanning System", 1973 Ultrasonics Symposium Proceedings, IEEE Cat. #73, pp. 43-48.

Freund et al., "Electronic Sector Scanning in the Diagnosis of Cerebrovascular Disease and Space-occupying Processes", vol. 23, Nov., 1973, pp. 1147-1159.

Freund et al., Recording Arterial Pulse Curves with Ultrasound-Experimental Investigations and Diagnostics Possibilities, *Proceedings in Echo-Encephalography,* 1968, pp. 193-196.

J. C. Somer, "Report on a Visit to Great Britain to Study", *Ultrasonics in Medicine* Apr., 1965.

J. C. Somer, Abstract "Electronic Sector Scanning for Ultrasonic Diagnosis," *Digest of the 7th Int'l Conference on Medical and Biological Engineering—Stockholm,* Aug. 16, 1967.

J. C. Somer, "Instantaneous and Continuous Pictures Obtained by a New Two-Dimensional Scan Technique with a Stationary Transducer," *Proceedings in Echo-Encephalopraphy,* Apr. 14, 1967.

J. C. Somer, Echo-Diagnostiek Technische Aspecten (not translated), Aug. 7, 1971, pp. 1347-1350.

J. C. Somer, et al., "An Electrically Variable Analogue Delay Line Achieved by Fast Consecutively Commutated Capacitors" *Progress Report* 3 (1972) *Inst. Med. Phys. TNO,* 1972, pp. 109-113.

Electronic Sector Scanning in Cerebral Diagnostics III. Visualization of Intracranial Structures and Brain Arteries" Presented at Proceedings at 2nd World Congress on Ultrasonics in Medicine, 1973, p. 305.

H. A. C., Kamphuisen, "Electronic Sector Scanning in Cerebral Diagnostics; II. Space Occupying Processes and Hydrocephalus" Presented at Proceedings at 2nd World Congress on Ultrasonic in Medicine, Rotterdam, Jun. 4-8, 1973.

Freund, H. J. "Electronic Sector Scanning in Cerebral Diagnostics III, Visualization of Intrcranial of Structures and Brain Arteries" presented at Proceedings at 2nd World Congress on Ultrasonics in Medicine, Jun. 4, 1973.

Somer and Oosterbaan, Abstract: "Ultrasonic Tomograhic Imaging of the Brain with and Electronic Sector Scanning System: Electroscan." Additional authors: 1974.

J. C., Somer, "Electroscan: An Eltronic Sector Scanning Method for Ultrasonic diagnostics", cardiovascular Applications of Ultrasound, (Chapter 31). From Proceedings of International Symposium, Belgium May 29-30, 1973, pp. 397-401.

Brendel, K. et al., "Methods of Measuring the Performance of Ultrasonic Pulse-Echo Diagnostic Equipment," Ultrasound in Medicine & Biology, vol. 2, 1976, pp. 343-350.

Somer, J. C., "Phased Array Systems," Echocardiology. pp. 325-334.

J. C. Somer, "Real-Time Improvement of Both Lateral and Range Resolution by Optical Signal Pr Presented at Ultrasonics Symposium Proceedings, pp. 1002-1005, 1977.

J. C. Somer, "Real-Time Improvement of Lateral and Rane Resolution by Optical Signal Processing," ab- (List continued on next page.)

OTHER PUBLICATIONS stract Proceedings of the British Medical Ultrasonic Society, Aug., 1978, p. 649.

J. C. Somer, Abstract: "Real-Time Improvement of Both Lateral and Range Resolution of Optica Processing", Presented at Ultrasonics Symposium, p. 259, 1978.

Manes, G. F., et al., "A new Technique with Application to Ultrasound Phased-Array Imaging System," Ultrasonics, vol. 17, No. 5 Sep., 1979.

Somer, J. C. et al., Abstract: Electroscan: Principle and Clinical Applications, Additional Author: Kamphusien, Dutch EEG Society., p. 439.

Williams, J. B., et al., "Versatile Echoscanner", *Ultrasound in Medicine*, vol. 2, Edited by White and Barnes, pp. 383-389.

Kapp, H., "A New Method of Echo-Pulse-Spygmography", Digest of the X International Conference on Medical and Biological Engineering, Edited by Albert R., et al., 1973 Session 227.

Somer, J. C. et al., "Electronic Sector Scanning with Ultrasound: Improvements and Clinical Results", *Digest of the 10th International Conference on Medical and Biological Engineering, 1973, p. 305.*

Somer, J. C., "Real-Time Improvement of both Lateral and Range Resolution by Optical Signal Processing" 1977 Ultrasonics Symposium Proceedings, IEEE Lat. #77CH1264-ISU, pp. 1002-1005.

Manes, G. F. et al., "A New Delay Technique with Application to Ultrasound Phased-Array Imaging Systems", *Ultrasonics*, vol. 17, No. 5 1979, pp. 225-227.

Somer, J. C. Abstract "Real-Time Improvement of Lateral and Range Resolution by Optical Signal Processing", *Proceedings of the British Medical Ultrasound Society*, 1978, p. 649.

Somer, J. C. Abstract, Real-Time Improvement of Both Lateral and Range Movement by Optical Signal Processing", Ultrasonics Symposium, 1978, p. 259.

Somer, J. C. et al., Abstract, "Ultrasonic Tomographic Imaging of the Brain with an Electric Sector Scanning System: Electroscan", Ultrasonics Symposium, 1974, p. 73.

Maslak, S. H. "An Electronically Steered Ultrasonic Transducer", Thesis submitted in partial fulfillment of the requirements for the degree of Doctor of Science, Massachusetts Institute of Technology, published prior to Apr. 5, 1976.

*Radar System Engineering*, Edited by L. Ridenour, McGraw-Hill Book Company, Inc. First Edition, Second Impression, 1947, pp. 164-167.

Cheston, T. C., et al., "Array Attennas", Chapter 11, *Radar Handbook*, Editor-in-chief M. Skolnik, McGraw-Hil, Inc., 1970, pp. 11-1 to 11-2.

Cheston, T. C., et al., "Phased Array Radar Attennas", Chapter 7, *Radar Handbook*, 2nd Edition, Editor-in-chiref M. Skolnik, McGraw-Hill Publishing Co., pp. 7.1, 7.7, 7.8.

Sahn, D. J. et al., "Multiple Crystal Echocardiography Evaluation of Endocardial Cushion Defect", Circulation, vol. 50, No. 1, Jul., 1974, pp. 25-32.

Hagan, A. D., et al., "Ultrasound Evaluation of Systolic Anterior Septal Motion in Patients with and without Right Ventricular Volume Overload", *Circulation*, 1973, pp. 248-254.

Sahn, D. J. et al., "Pediatric Echocardiography: A review of its clinical utility", *The Journal of Pediatrics*, vol. 87, No. 3, Sep., 1975, pp. 335-352.

Popp, R. L. et al. "Diagnostic Accuracy of an Ultrasonic Multiple Transducer Cardiac Imaging System", American Heart Journal, vol. 90, No. 3, Sep. 1975, pp. 329-334.

Donald K. King, M.D., "Cardiac Ultrasonography, A-Stop-Action Technique for Imaging Intracardiac Anatomy," *Radiology, vol.* 103; May, 1972, No. 2, p. 387-392.

Donald L. King, M.D., et al, Left Ventricular Volume Determination by Cross-Sectional Cardiac Ultrasonography," *Radiology vol.* 104; Jul, 1972, No. 1., pp. 201-202.

Donald L. King. M.D., "Renal Ultrasonography," *Radiology, vol.* 105, Dec., 1972, pp. 633-640.

Donald L. King, M.D., Cardiac Ultrasonography, Cross Sectional Ultrasonic Imaging of the heart," *Circulation, Vol. XLVII*; Apr. 1973, pp. 843-847.

Donald L, King, M.D., et al., "Demonstration of Transposition of the Great Arteries by Cardiac Ultrasonography," *Radiology, vol.* 107., Apr., 1973., pp. 181-186.

Donald L. King, M.D., "Real-Time Cross-Sectional Ultrasonic Imaging of the Heart Using a Linear Array Multi-Element Transducer," *Journal of Clinical Ultrasound*, vol. 1, No. 3; Sep., 1973., pp. 196-200.

Donald L. King, M.D., *Diagnostic Ultrasound*, edited by (List continued on next page.)

OTHER PUBLICATIONS

King. Chapter 2: Physical and technical princciples., 1974.

Donald L. King, M.D., *Diagnostic Ultrasound*, edited by King, Chapter 5: Echo-cardiography in acquired heart disease, 1974.

Donald L. King, M.D., et al., "Diagnostic Ultrasound of the Urinary Tract," *Journal of Clinical Ultrasound*, vol. 4, No. 1. 1974, pp. 55-64.

Donald L. King, M.D., et al., "Diagnostic Ultrasound of the Urinary Tract," *Journal of Clinical Ultrasound*, vol. 4, No. 1, 1975.

Donald L. King, M.D., et al., "Optimal Resources for Ultrasonic Examination of the Heart," The American Journal of Cariology, vol. 35, Jun. 1975, No. 2.

Donald L. King, M.D., et al., "Technique for Dual Transducer Echocardiography," *Journal of Clinical Ultrasound*, vol. 4, Nov., 1975, No. 2., pp. 139-140.

Donald L. King, M.D., et al., "Augmentation of auscultatory and echocardiographic mitral valve prolapse by atrial premature depolarizations," *American Heart Journal*, Annotations, vol. 93, Apr., 1977, No. 4., pp. 533-535.

Donald L. King. M.D., et al., "Outflow Tract Obstruction in Tetralogy of Fallot, Intraoperataive analysis by echocardiography," *New York State Journal of Medicine*, Jun., 1978.

Donald L. King, M.D., et al., "Ultrasonography of the Primary Cysts of the Liver," *American Journal of Roentgenol*, vol. 131, No. 2. Aug., 1978.

Donald L. King, M.D., et al, "Mobile Intracardiac Varix: A New Enchocardiographic Entity," *American Journal of Roentgenal*, vol. 138, Mar., 1982.

Barnes and Thurstone, *An Ultrasound Moving Target Indicator System for Diagnostic Use*, IEEE Transactions on Bio-medical Engineering, Jan. 1971 pp. 4-8.

Fox, et al., *Spherical Aberration in Long Wavelength Holography*,. Acoustical Holography, vol. 4, 1972, pp. 501-518.

Miller et al., *A study of Near Field Ultrasonic Beam Patterns from a Pulsed Linear Array*, Acoustical Holography, vol. 5, 1973, pp. 261-281.

Kisslo, et al., *Thaumascan; Clinical Cardiac Imaging*, Ultrasound In Medicine, vol. 1.

Smith et al., *Schlieren Study of Pulsed Ultrasound Transmission Through Human Skull*, Journal of Clinical Ultrasound, vol. 2, No. 1, 1974, pp. 55-59.

Kisslo, et al., *A Phased Array Ultrasound System for Cardiac Imaging*, Proceedings, 2nd European Congress on Ultrasonics in Medicine, Excerpta Medica Amsterdam, 1975, pp. 67-74.

von Ramm, et al., Application of Optical Instrumentation in Medicine III, 1975 47:93-95.

Philips, et al., *Sampled Aperture Techniques Applied to B-Mode Echoencephalography*, Acoustical Holography, vol. 6, 1975 pp. 103-120.

Duke University Film script, Dec., 1975.

Kisslo, et al., *Echocardiographic Evaluation of Tricuspid Valve Endocarditis An M Mode and Two Dimensional Study*, The American Journal of Cardiology, vol. 38, Oct. 1976, pp. 502-507.

von Ramm, et al., *Cardiac Imaging Using a Phased Array Ultrasound System*, Circulation, vol. 53, No. 2, Feb. 1976, pp. 258-267.

Kisslo, et al., *Clinical Results of Real-time Ultrasonic Scanning of the Heart using a Phased Array System*, The Yale Journal of Biology and Medicine, 1977, pp. 355-365, presented at the National Meeting on Diagnostic Ultrasound, Jul., 1976.

Kisslo, et al., *Dynamic Cardiac Imaging Using a Focused, Phased-array Ultrasound System*, The American Journal of Medicine, vol. 63, 1977, pp. 61-68.

Kisslo, et al., *Quantitative Validation of Left Ventricular Targets by Two-dimensional Echocardiography*, Abstracts of the A.H.A., 50th Scientific Session, Oct., 1977, p. III-153.

Smith, et al., *Real Time Ultrasound Tomography of the Adult Brain*.

von Ramm, et al., *A Multiple Frequency Array for Improved Diagnostic Imaging*, IEEE Transactions on Sonics and Ultrasonics, vol. SU-25, No. 6, 1978.

Kisslo, et al., *Dynamic Cardiac Imaging using a Phased-Array Transducer System*, 1975, pp. 45-49.

von Ramm et al., *Thaumascan: Improved Image Quality and Clinical Usefulness*, Ultrasound in Medicine, vol. 2, 1975, pp. 463-464.

von Ramm, *Real Time Two Dimensional Ultrasound Imaging*, Proceedings of the 6th New England Bioengineering conference, Mar. 23-24, 1978, pp. 262-265.

(List continued on next page.)

OTHER PUBLICATIONS

Kissler et al., *Techniques for Real-time Two-Dimensional Echocardiography*, Clinical Echocardiography, 1978, pp. 21-38.

Thurstone, F. L., "Electronic Beam Scanning applied to Dynamic Cardiac Imaging", *Cardiac Ultrasound*, Edited by Gramiak & Waag, Chapter 16, pp. 239-244, 1975.

Organon Teknika brochure regarding ECHOMATIC automatic single-element system for Echocardiology.

Organon Teknika brochure "Diagnostic Ultrasound-Unequaled resolution, Features and Flexibility."

Dr. Nicholas Bom, Organon Teknika Service Manual regarding ECHO$^{cardio}$VISOR 03, ECHO VISOR and ECHO$^{bio}$VISOR.

Dr. Nicholas Bom et al., "Ultrasonic Viewer for Cross Sectional Analysis of Moving Cardiac Structures," *BioMedical Engineering*, Nov., 1971.

Dr. Nicholas Bom, *New Concepts in Echocardiography*, 1972, pp. 9-98.

Dr. Nicholas Bom et al., "An Ultrasonic Intracardiac Scanner," *Ultrasonics*, Mar., 1972, pp. 72-76.

Dr. Nicholas Bom, "A Non-Invasive Method for Two Dimensional Instantaneous Observation of Moving Carciac Structures," *New Concepts in Echocardiography*, Chapter IV, May 24, 1972.

Roelandt et al., "Multiscan Echocardiography, Description of the System and Initial Results in 100 Patients," *Hart Bulletin*, 1973, pp. 51-56.

Organon Teknika brochure regarding ECHO$^{cardio}$VISOR 01, Instantaneous two-dimensional visualization of the heart in motion, 1973.

Dr. Nicholas Bom et al., "Multi-Element System and Its Application to Cardiology." Presented at 2nd World Congress on Ultrasound in Medicine, Jun. 4, 1973, pp. 297-299.

Dr. Nicholas Bom et al., "Multiscan Electrocardiography I. Technical Description," *Circulation*, vol. LVVIII, Nov., 1973, pp. 1066-1074.

Kloster et al., "Multiscan Electrocardiography II. The Technique and Initial Clinical Results,: *Circulation*, vol. XLVIII, Nov., 1973, pp. 1075-1084.

Dr. Nicholas Bom et al., "Two Multi-Element Systems for Real Time Cross-Sectional Analysis of the Heart," presented at IEEE Ultrasonic Symposium, Nov. 5, 1973.

Roelandt et al, "Multidimensional Echocardiography, An Appraisal of its Clinical Usefulness," *British Heart Journal*, 1974.

Roelandt et al., "Ultrasonic Cross-Sectional Study of the Heart in Motion Present Possibilities and Perspectives," *Triangle*, vol. 13, No. 4, 1974, pp. 139-149.

Dr. Nicholas Bom et al., "Evaluation of Structure Recognition with the Multiscan Echocardiography," *Ultrasound in Medicine & Biology*, vol. I, 197, p. 243.

Roelandt et al., "Multiscan Echocardiography," *Cardiovascular Applications of Ultrasound*, May 29, 1973, pp. 402-418.

Dr. Nicholas Bom, Abstract "Two Multi-Element Systems for Real Time Cross-Sectional Analysis of the Heart," *IEEE Transactions on Sonics and Ultrasonics*, vol. SU-21, No. 1, Jan., 1974, pp. 61, 68-69.

Dr. Nicholas Bom et al., "A Multielement System in Cardiac Imaging," *Cardiac Ultrasound*, Chapter 18, 1975, pp. 255-263.

Lancee et al., "Construction of a Circular Array with Miniature Elements for Cardiac Application," *Proceedings of the Second European Congress on Ultrasonics in Medicine*, May 12, 1975, pp. 49-53.

Dr. Nicholas Bom et al., "The Technology of Miniature Acoustic Element Arrays," *Cardiovascular Imaging and Image Processing*, vol. 72, Jul., 1975, pp. 11-15.

Vogel et al., "Automation in Processing of Echocardiographic data," *Computers in Cardiology*, Oct. 2, 1975.

Sahn et al., "A dual M-mode system for simultaneous time motion analyses of cardiac structures and evaluation of cardiac function: initial clinical applications," *Echocardiology*, 1977, pp. 83-93.

Organon Teknika Operating Manual regarding Fociscan ECHO$^{cardio}$VISOR, 1978.

Organon Teknika Operating Manual regarding Sector Scanner, 1978.

J. Roelandt, Echocardiography: Current Applications of Echotechniques in Cardioiogy, *Hart Bulletin*, Feb., 1975, pp. 9-20.

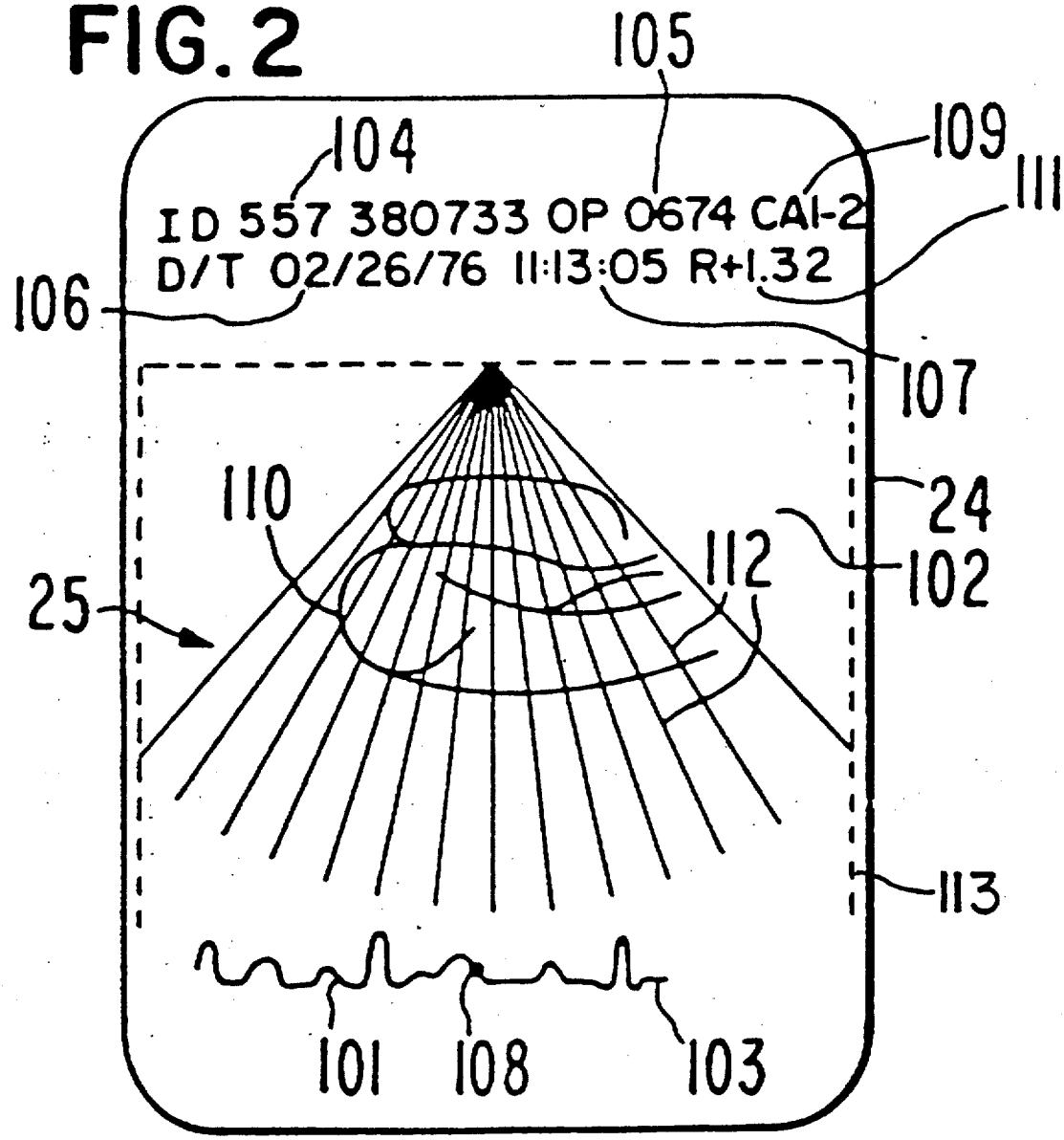

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 15, lines 18-38:

It might be pointed out here that the indicator marks 113 of FIG. [3] *2* comprise a series of marks spaced at intervals corresponding to one centimeter distances within the human body. These indicator marks provide valuable assistance to the diagnostician in judging the size and spacing of structures being observed in the image 110. These indicator marks are generated in Master Control logic 114 (FIG. 1) and are displayed on both the visual display 24 and slave scope 28 during the frame overhead interval between B-scans. They are thus preserved by the photographic record made by camera 32 or video record made by video recorder 40. Since the size of the image may vary depending upon the enlargement of the photographic or video display image, it is important to have suitable calibrations that relate the final image to the actual size of the original structures. Sector size control 156 may also be used to change the size of the displayed image, however master control logic 114 takes this size information into account and provides the appropriate scaling of indicator marks 113.

The drawing figures have been changed as follows: Reference numeral 113 has been added to FIG. 2.

AS A RESULT OF REEXAMINATION, IT HAS BEEN DETERMINED THAT:

The patentability of claims 1-2 and 7-8 is confirmed.

Claims 3-6, 9-11, 13 and 15-17 are cancelled.

Claims 12 and 14 are determined to be patentable as amended.

New claim 18 is added and determined to be patentable.

12. A system in accordance with claim [10] *18* wherein said operator-viewable display comprises a CRT.

14. A system in accordance with claim 13, *wherein said first means is a phased array means and further including TM recording means for simultaneously effecting a TM recording of said two-dimensional real-time display image with the displaying of said two-dimensional real-time image.*

*18. An ultrasonic system of the type utilized in patient cardiac and cardiovascular diagnosis comprising:*

*first means including a multi-element transducer for generating and displaying a fan shaped two-dimensional real-time operator-viewable image on an operator-viewable display of a patient region being examined from ultrasonic energy directed into said patient by said transducer and reflected out of said region into said transducer, whereby said two-dimensional real-time image is generated by said first means;*

*ECG recording means operatively associated with said first means, and being connected to said patient being examined, for generating an ECG output from said patient, said ECG recording means comprising means for displaying said ECG output as a real-time ECG trace on said operator-viewable display for a patient being examined and means for refreshing at least a portion of said ECG output on said operator-viewable display thereby enabling persistence of said ECG output for study by said operator;*

*said means for refreshing comprising means for digitizing said ECG output to provide digitized values of said ECG output, memory means for storing digitized values, means for reading out the stored values from storage addresses in said memory means, and means for converting the read-out values whereby said ECG output is generated on said operator-viewable display means; and*

*means associated with said means for reading out the stored values, for correlating the storage addresses of said stored values and the read-out thereof with the occurrence of an R-wave in said ECG output.*

* * * * *